United States Patent [19]

Yman

[11] Patent Number: 4,642,232
[45] Date of Patent: Feb. 10, 1987

[54] FORMULATED ALLERGEN PREPARATION AND ITS USE

[75] Inventor: Rolf L. Yman, Upsala, Sweden

[73] Assignee: Pharmacia AB, Upsala, Sweden

[21] Appl. No.: 709,033

[22] PCT Filed: Jun. 15, 1984

[86] PCT No.: PCT/SE84/00227
§ 371 Date: Jan. 28, 1985
§ 102(e) Date: Jan. 28, 1985

[87] PCT Pub. No.: WO85/00015
PCT Pub. Date: Jan. 3, 1985

[30] Foreign Application Priority Data

Jun. 15, 1983 [SE] Sweden .................... 8303401

[51] Int. Cl.$^4$ .................... A61K 9/24; A61K 39/00
[52] U.S. Cl. .................... 424/19; 424/21; 424/88; 424/89; 424/91; 424/92; 514/456
[58] Field of Search .................... 424/88, 91, 19, 21; 514/456

[56] References Cited

U.S. PATENT DOCUMENTS

| | | | |
|---|---|---|---|
| 3,224,942 | 12/1965 | Martin | 424/88 |
| 4,158,705 | 6/1979 | Malley | 424/88 |
| 4,215,036 | 7/1980 | Malley | 424/88 |
| 4,314,993 | 2/1982 | Wijnendaele | 424/88 |
| 4,409,237 | 10/1983 | Cairns et al. | 514/456 |
| 4,457,913 | 7/1984 | Kokubu | 424/88 |
| 4,473,548 | 9/1984 | Frenkel | 424/88 |

OTHER PUBLICATIONS

Stemmann et al—Prax. Pneumol., vol. 33, (1979) pp. 302–304.
Roitt—Essential Immunology–4th edit., (1980) Blackwell Science Publicat., pp. 217–252.

*Primary Examiner*—Sam Rosen
*Attorney, Agent, or Firm*—Fred Philpit

[57] ABSTRACT

The invention is concerned with a formulated preparation to be used for oral administration and containing an immunotherapeutically active amount of at least one allergen. The characteristic feature of the invention is that said formulated preparation is resistant to gastric juice and contains an antiallergic substance.

10 Claims, No Drawings

FORMULATED ALLERGEN PREPARATION AND ITS USE

The present invention is concerned with a novel formulated preparation containing an immunotherapeutically active amount of at least one allergen. The invention comprises also a method of treating allergic conditions by oral administration of the formulated preparation.

Allergic disorders may arise when the body is exposed to foreign substances, for instance due to inhaling of such substances or due to their contacting the skin or mucous membranes, or due to their reaching the body via the food ingested. Hypersensitivity reactions may occur, resulting from stimulation of immunological or other mechanisms.

The term "allergen" is used here and subsequently to mean a substance which, when exposed to a mammal, will be able to mount an immune response resulting in antibodies of the IgE-class and which also will be able to trigger an allergic reaction when the mammal later on is exposed to the substance. Allergens are chemically a very heterogenous class of compounds and they may consist of protein, a lipid, a carbohydrate or a combination thereof such as a glycoprotein, a proteoglucan, a lipoprotein etc.

Some compounds eliciting allergenic activity have to combine with biopolymers in vivo in order to mount the immune response or to trigger the allergic reaction in question.

Among immunologically-based disorders, the most dramatic one is the so-called atopic or IgE mediated allergic reaction which in its most severe form may result in a so-called anaphylactic shock which is potentially fatal. This disorder is characterized by the presence of antibodies of the immunoglobulin E class (IgE) which are capable of binding just that foreign substance (allergen) to which the individual is hypersensitive. These IgE antibodies moreover have the property of binding to the surface of certain cell types in the body. One such cell type is the mast cell which is present abundantly in the skin and in the mucosae of e.g. the nose, eyes, trachea and intestine.

When IgE antibody coated mast cells are exposed to the allergen that had originally "raised" the antibody, the mast cells are stimulated to release so-called mediators. All these mediators, for example histamine, SRS-A (leucotrienes), PAF (platelet activating factor) and a number of chemotactic factors and enzymes, contribute to the typical allergic inflammation which is characterized by (i) an early phase starting immediately with edema, contraction of smooth muscles and increased secretion, and (ii) a late phase with infiltration of phagocytic cells.

There are different ways of alleviating an allergic condition. Two of these are utilized in accordance with the present invention, viz.:

(1) Immunotherapy, also called hyposensitization, whereby the aforesaid stimulation of the mast cell may be prevented, probably due to a combined effect of developing immunological tolerance (inhibiting IgE antibody formation) and forming so-called blocking antibodies which belong to other classes of immunoglobulins.

(2) Pharmacotherapy, by which allergic symptoms may be averted or mitigated. Averting of the symptoms may be obtained by means of mediator release inhibition (for instance by administration of antiallergic substances such as e.g. disodium cromoglycate (DSCG) or other substances which applied locally are apt to decrease or prevent mediator formation or release, such as e.g. calcium antagonists, substances increasing the CAMP level or substances interfering with leucotriene synthesis). Mitigation of the symptoms may be obtained by inhibition of the effect of the mediators (for instance by administration of antihistamine or of antagonists to other mediators or of substances having opposite effects such as e.g. adrenergics, anticholinergics or xanthine derivatives).

An antiallergic substance of the DSCG type is believed to locally affect the mast cell so as to inhibit release of histamine and other mediators of the immediate allergic reaction. To be effective the drug has to reach the mast cell prior to the exposure to allergen. Ever since the discovery of DSCG, attempts have been made to find other compounds inhibiting this reaction. Ketotiphene, for instance, has been said to be such a potential compound. But unfortunately, such potentially promising substances are very rarely as effective in actual fact as they have seemed to promise.

The term "antiallergic substance" is used here and subsequently to mean a substance inhibiting the allergen-induced allergic and inflammatory reaction. Consequently such "antiallergic substances" should be understood to comprise substances inhibiting mediator release as well as substances neutralizing the mediators themselves.

Immunotherapy means that an allergy patient is treated with small amounts of the allergen to which he is allergic, the purpose of this treatment being that the patient is to build up a defense or tolerance in action the next time he is exposed to that particular allergen. Thus the object is to prevent the allergen from binding to its specific IgE antibodies on the mast cell. In immunotherapy treatment, the patient is given repeated administrations of (immunotherapeutically active amounts of) allergen to thereby build up his defense. However, the doses must not be so high as to give rise to an allergic reaction. It will therefore be appreciated that immunotherapy implies a precarious balancing between the administration of an effective dose and the prevention of an anaphylactic reaction.

Immunotherapy is normally carried out by means of subcutaneous injections of allergen. For certain food allergies it has, however, been suggested that the normal route of the allergen should be utilized, thus comprising oral administration and absorption in the stomach or intestine. It has been suggested also, in this context, that the hyposensitizing treatment should be combined with DSCG administration.

Thus in connection with food allergies oral hyposensitization combined with oral administration of DSCG has been previously known. The role of DSCG was believed to reside in exerting its effect locally in the digestive tract, i.e. in the zone where exposure to the allergen takes place. Tests have been carried out in which food allergy patients have been given 180-300 mg of DSCG for 3-10 days before allergenic challenge (La Nouv. Presse Méd. 8, (1979):22, p. 1851-52). These tests have ultimately resulted in a proposal for an oral hyposensitizing method which is quite rudimentary and involves many disadvantages. The teachings of the reference are conducive to a hyposensitizing method in which exposure to the allergen and ingestion of DSCG take place at entirely different times. This is unpractical because the digestive functions of the stomach and intestine are apt to vary from individual to individual and at different occasions in one individual. Moreover it has been found to be difficult, with concomitant risks, to persuade participant indidividuals to repeatedly ingest two different preparations at different occasions; it should be noted here that deviations from a strict dose administration schedule entrain the risk of an anaphylactic reaction. The obstacles of the prior art methods for oral and/or intestinal hyposensitization are mainly the same as for skin hyposensitization. Even in a very weak allergy there is always a risk for an anaphylactic reaction. Once adverse reactions have been initiated their further development is hard to control.

Capsules containing allergen and intended for oral administration have also been described by Stickl, H. and by Stickl. H. conjointly with Kersher, G. (Fortschr. Med. 99 (1981), p. 1991-3, and 16th 98 (1980), p. 343-46, respectively). However, unpublished results (Björksten, B.) have shown that oral administration of allergen capsules may give rise to side effects in the form of diarrheas and other unpleasant phenomena. The work of both Björksten and Stickl has been directed towards immunotherapy irrespective of whether or not the allergen is a foodstuff.

Earlier on, attempts have been made also with so-called peroral hyposensitization. According to this method dilute solutions of the allergen have been placed under the patient's tongue. The method has been found to be virtually ineffective.

From what has been said above it will be evident that there is a great need of novel formulated preparations and improved methods for non-parenteral hyposensitization. Such preparations and such methods are provided by the present invention which is aimed at eliminating the aforesaid disadvantages inherent in the earlier methods and preparations. The greatest advantage provided by the invention is that the immunotherapeutic dose can now be increased considerably without any significant increase of the risk of provoking an anaphylactic reaction. The present invention will enable, for intestinal hyposensitization purposes, to administer the correct dose of the allergen preceded by a protective dose of an antiallergic substance at the correct location with a predetermined time lag between delivery of the protective compound and the allergen.

The formulated preparation according to the invention is characterized by being resistant to gastric juice and containing a therapeutically active amount of an antiallergic substance. The preparation is intended for oral administration, and in a preferred embodiment is characterized in that upon being administered it gives a delayed release of both the active amount of the antiallergic substance and the immunotherapeutically active amount of the allergen so that both of these are released, in the order as stated, when exposed to the action of intestinal juice while remaining unreleased under the action of gastric juice. By "resistant to gastric juice" is meant that the preparation resists attack by gastric juice, so that a therapeutically active amount of both the allergen and the antiallergic substance can pass through the stomach and be released in the intestine. The concept of "resistance to gastric juice" is widely known and accepted, and this term has been in use for almost a century.

The invention also comprises a method for intestinal immunotherapy treatment of allergies, in the first place IgE mediated allergies. According to this method a formulated preparation of the type as set forth above is administered orally to a patient who is allergic to the allergen in said preparation. The invention is in particular concerned with a method, and a preparation formulated therefore, which during intestinal immunotherapy will inhibit the allergic reaction, especially the immediate allergic reaction.

The term "intestinal immunotherapy" means that the treatment is carried out by causing the allergenic material to be delivered to and absorbed in the intestine. This type of hyposensitization is not restricted to the case where the allergen is one that is present in a foodstuff: also other allergens may be employed.

The most important allergens to be used according to the invention are the so-called food allergens and inhalation allergens. This types of allergens are of proteinaceous nature having more than one antigenic determinant and a molecular weight of more than 2000 daltons, either in itself or combined with body proteins. Examples of low molecular weight allergens are drugs, such as penicillin, and reactive chemicals. The proteinaceous allergens are mostly used in the form of extracts, which are derived from their natural sources. Common proteinaceous allergens are found in dust, mites, plants, animals, fungi, insects and insect venoms, food etc.

In the light of experience made to date, the most preferred antiallergic substance to be employed according to this invention is of the type which inhibits mediator release. Examples are disodium cromoglycate, homologues and analogues thereof, and other therapeutically active and pharmaceutically acceptable salts, esters or amides of the corresponding acids. The invention also covers substances which will be found later on to have the same effect as DSCG ("DSCG effect"); compounds of the DSCG-type are described in U.S. Pat. No. 3,419,578. They are called Bis-Chromonyl compounds and have the general structure:

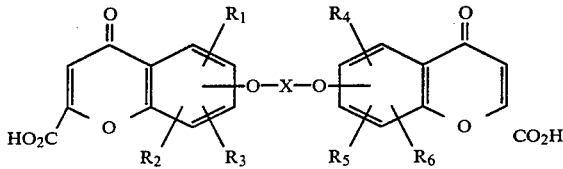

wherein $R_1$, $R_2$, $R_3$, $R_4$, $R_5$ and $R_6$ are the same or different and each is H or halogen, lower alkyl, hydroxy, lower alkoxy, substituted lower alkyl or substituted lower alkoxy, and X is a saturated or unsaturated, substituted or unsubstituted, straight or branched polymethylene chain which may be interrupted by one or more carbocyclic rings or oxygen-containing heterocyclic rings, oxygen atoms or carbonyl groups.

The advantages of the invention are in the first place derived from the fact that (i) the allergen and (ii) the antiallergic substance are administered in the form of one formulated preparation in which both (i) and (ii) are present. The invention enables a therapeutically active amount of the antiallergic substance to be administered locally to the intestine. Local release of a therapeutically active amount of the antiallergic substance takes place within a well-defined period of time before the allergen becomes available for producing an anaphylactic response.

The formulated preparation according to the present invention enables antiallergic substance to be relased as soon as it has reached the intestine; but also earlier. In this latter case, however, it is imperative that a therapeutically active amount of the substance still remains in the formulated drug preparation so that it can be released therefrom when the preparation reaches the intestine. Normally the antiallergic substance or most of it should be released within 60 minutes after arrival of the formulated preparation in the intestine, and most preferably within 30 minutes.

Allergen should not be released from the preparation before the latter has reached the intestine. The allergen release in the intestine may then start when an active amount of the antiallergic substance has been released and become effective. In actual practice the allergen should be released within 120 minutes after arrival of the preparation in the intestine, preferably within 30 minutes after the bulk of the antiallergic substance has been released from the preparation in the intestine. The dissolution rate is defined by the conditions prescribed for simulated intestinal juice in the US Pharamcopoea XX, p. 1105, and its third supplement p. 310-11.

For each dosage unit of the formulated preparation, the total amount of allergen and the total amount of antiallergic substance may vary. The same applies to their proportions inter se. A substance having a low antiallergic effect can be combined with only small amounts of allergen. Highly potent allergens will require larger amounts of antiallergic substance. DSCG is regarded as being non-toxic in itself and so may be administered in unlimited amounts. Other substances exhibiting an antiallergic effect may give rise to side reactions, and consequently each dosage unit may contain only small amounts of these active substances. It is important, however, that the amount of antiallergic substance per unit dose is always such in relation to the amount of allergen per unit dose that it will inhibit any potential allergic reaction in the intestine. To an average person skilled in the art it will be quite easy to ascertain the proper proportions and amounts that are acceptable. A point to be noted here is of course that a patient may become sick if proportions are chosen wrongly.

As regards the volume of the dosage unit, its upper limit is set by that which can be swallowed. As a rule this means that each unit will always contain less than 500 mg of the antiallergic substance. The upper limit for the amount of allergen is set by the ability of the antiallergic substance to protect the patient from an anaphylactic reaction; usually the amount of allergen per dosage unit is from 1 to 500 mg. In immunotherapy it is common practice to start with a low dose of allergen. After this and as the treatment is proceeding further, it is possible as a rule to increase the dose administered and consequently there may be a need of dosage units having different contents of allergen. A further corollary is that even in a single individual the immunotherapeutic amount for any given allergen may differ in different stages of therapy. Of course the immunotherapeutic dose is affected also by purification and enrichment, as well as in some cases chemical or physical modifications carried out for the purpose of increasing or decreasing the allergenicity of the allergenic material.

When a plurality of different allergens are combined in a single formulated preparation due attention must be paid to their relative potencies and to such immunological cross reactivities as may sometimes occur.

The preparations according to the invention may take various different pharmaceutical forms. Examples of advantageous forms are double-wall capsules, two-layer tablets and combinations thereof. Double-wall capsules may contain the allergen in their interior (core capsule, core) and contain the antiallergically active substance in the space between their walls (=in their envelope). Two-layer tablets may contain the anti-allergically active substance in their outer layer (=envelope) and contain the allergen in their interior (=core). Capsule walls and/or layer surfaces may advantageously be coated with a film resistant to gastric juice or other film to thus become more resistant to gastric juice attack or acquire more well-defined and predetermined release properties. Coating of the core will cause a delay in the release of the core contents. If a thicker coating is applied on the core the release of the allergen will be delayed still further in relation to the release of the antiallergic substance. Other types of preparations, too, may be used, such as for instance tablets containing microcapsules with allergens spread in and surrounded by the substance having an antiallergic activity. In its broadest concept the invention comprises any and all forms for administration that give a delayed intestinal release of both the antiallergic substance and the allergen so that immunotherapy may proceed under the protection of the antiallergic substance.

The formulated preparation according to the invention may contain both the allergen and the antiallergic substance together with pharmaceutically acceptable adjuvants, carriers and additives. All of these three types of additional ingredients are well-known to persons skilled in the art. The allergen is usually employed as an extract in a freeze-dried form.

Capsules and tablets which are resistant to gastric juice and have predetermined release properties in intestinal juice may be produced according to known techniques ("The Theory and Practice of Industrial Pharmacy", Lachman L., Lieberman H. A. and Klanig J. L., 2nd edition Lea F. Febiger, Philadelphia, USA (1976), p. 321-465). Capsules of suitable sizes are commercially available. They are usually composed of gelatin or other material that will be unaggressive in the digestive tract. Filled capsules and compressed tablets are rendered resistant to gastric juice by being coated with a film of resistant material. The material of the envelope or shell of the capsule will be a further factor contributing to determining the rate of dissolution. One may thus choose, for example, a gelatin dissolving at the pH of the intestinal juice while remaining undissolved at the pH of the gastric juice. In that case there will be less need to apply a coating of a film which is resistant to gastric juice. In cases where a coating is applied this will be done with the coating material dissolved in a volatile solvent. Materials that are resistant to gastric juice are commercially available from a multitude of commercial sources. Such materials may consist of e.g. non-toxic cellulose esters and synthetic polymers. The materials that are useful in the context of the present invention are capable of dissolving in intestinal juice having a pH higher than 3, preferably higher than 5, depending on where, i.e. in which intestinal region or zone, release is desired.

In the light of experience made to date, the most preferred modality of the invention is an enteric coated formulation containing a proteinaceous allergen in combination with the antiallergic substance DSCG.

The invention is not in any way limited to the forms of administration mentioned above, although capsules and tablets are currently being regarded as having certain practical advantages. The below examples are set forth for the purpose of illustrating the invention and should not be construed as limiting the scope thereof.

EXAMPLE 1

Double capsule resistant to gastric juice and containing an antiallergic substance as well as egg allergen

Capsule 10 g of powdered egg albumen were subjected to briquetting, trituration and screening to 20 mesh, whereupon the thus resultant particles were uniformly distributed into 100 gelatin capsules No. 5 (0.13 ml standard capsule from Parke-Davis, USA). Each capsule was sealed and enclosed together with 100 mg disodium cromoglycate (DSCG) in a gelatin capsule No. 2 (0.37 ml standard capsule from Parke-Davis, USA). The outer capsules were then sealed and pan coated with a gastric juice resistant film material; this was applied in the form of a solution corresponding to that set forth in Example 4 (D).

Simulated gastric juice (US Pharmacopoea XX p. 1105 and its supplement 3 p. 310–11) was employed for checking the gastric juice resistance of the double capsule obtained (2 h).

In an analogous manner, double capsules were produced in which the DSCG was replaced by glucose.

Components dissolved out

The rate at which DSCG and egg albumen allergen were dissolved out was measured in a bath of intestinal juice in accordance with US Pharmacopoea XX p. 1105 and its supplement 3 p. 310–11, with determination of changes in protein concentration and in the light absorption of the bath at 325 nm (DSCG). Changes in protein concentration were determined according to the method of Bensadoun and Winstein, Analytical Biochemistry 70 (1976), p 241. The changes, expressed as a function of time, are set forth in Table 1a below:

TABLE 1a

| Time, min. | Release in intestinal juice, % | |
|---|---|---|
| | DSCG | allergen |
| 0 | 0 | 0 |
| 15 | 10 | 2 |
| 20 | 26 | 4 |
| 25 | 33.5 | 11 |
| 30 | 52 | 19 |
| 35 | 78 | 29 |
| 40 | 87 | 40 |
| 50 | | 54 |
| 60 | | 62 |
| 80 | 100 | 78 |

EXAMPLE 2

A series of double blind tests was run on egg hypersensitive patients to verify the proper performance of the preparation in vivo, that is, to verify that allergen can thus be supplied to the patients without causing the local or general allergic reaction that would have followed upon traditional administration of a corresponding dose of the allergen.

The patients were given capsules produced according to Example 1. These were either capsules containing egg albumen allergen together with DSCG or, respectively, capsules containing the egg albumen allergen but having the antiallergic agent replaced by glucose. The results are given in Table 2. The preparation of Example 1 releases allergen at a time interval of 15 min. (average) after DSCG release.

TABLE 2

| | Clinical symptoms after administration of | |
|---|---|---|
| Patient | Formulated preparation (egg albumen allergen + DSCG) | Control preparation (egg albumen allergen + glucose) |
| A | no reaction | vomiting abdominal pain |
| B | no reaction | (not done) |

It can be seen from these tests that by using combination capsules containing both the antiallergic substance and the allergen it is possible to reduce the risk of anaphylactic reactions occurring in the course of intestinal immunotherapy.

EXAMPLE 3

Double capsules resistant to gastric juice and containing antiallergic substance as well as timothy grass pollen allergen 100 double capsules were produced in a manner similar to that of Example 1. Each capsule contained an inner capsule with 10 mg pollen of timothy grass (Phlemum pratense) and surrounded by 100 mg DSCG.

The antiallergic substance and allergen were dissolved out in a manner analogous to Example 1. Also as in Example 1, DSCG was measured as the change in final absorption at 325 nm. The changes occurring in the allergen activity of the bath (activity of timothy grass pollen) were measured by RAST inhibition, (Yman et al., Develop. biol. Stand. 29 (1975), p. 151–165), as modified according to Schröder and Yman, (Allergy 35 (1980), p 234–236). It will be seen from Table 3 how the antiallergic and allergen substances were dissolved out successively.

TABLE 3

Release of DSCG and timothy grass pollen allergen from double capsule

| Time, min. | Release in intestinal juice, % | |
|---|---|---|
| | DSCG | allergen, *Phleum pratense* |
| 0 | 0 | 0 |
| 10 | 4 | 0 |
| 20 | 21 | 2 |
| 30 | 68 | 10 |
| 40 | 89 | 40 |
| 50 | | 60 |
| 60 | 100 | 75 |

EXAMPLE 4

Antiallergic Substance and Allergen in Double Tablet (Compressed Dragée) Resistant to Gastric Juice Ingredients per tablet produced:

| | 1 tablet |
|---|---|
| A. Core | |
| Powdered egg albumen (grade P:26 from Kallbergs Industri AB, Toreboda, Sweden) | 100 mg |
| Avicel ® (Ph 102, microcrystalline cellulose, FML International, Cork, Ireland, see also Merck Index 8th edition, Merck Co. Inc., Rahway, USA (1976) p. 246) | 18 mg |
| Aerosil ® (silica particles, 2 nm, from Degussa, Federal Republic of Germany) | 1 mg |
| Magnesium stearate | 1 mg |
| B. Envelope | |

-continued

| | 1 tablet |
|---|---|
| Disodium cromoglycate (DSCG) | 100 mg |
| Avicel ® | 98 mg |
| Aerosil ® | 1 mg |
| Magnesium stearate | 1 mg |
| C. Gastric juice resistant film, core | |
| Eudragit ® L100 (esters of polymethacrylic acid, Rohm & Haas GmbH, Darmstadt, Germany) | 10 mg |
| *Ethanol 99.5% | 73 mg |
| *Acetone | 73 mg |
| Citroflex 4 ® (softener, Pfizer, USA) | 6 mg |
| Propylene glycol | 3 mg |
| D. Gastric juice resistant film, compressed dragee | |
| Eudragit ® L100 | 30 mg |
| *Ethanol 99.5% | 219 mg |
| *Acetone | 219 mg |
| Citroflex 4 ® | 17 mg |
| Propylene glycol | 9 mg | evaporates and will not be present in the final product.

100 core tablets were prepared by introducing the item (A) materials into a mixer and mixing them homogeneously. Brilliant Blue was added as a marker to permit observation of allergen release from the tablet. The mixture was then compressed to tablets, and these were pan coated with a solution according to (C) above, whereby they were coated with a gastric juice resistant film.

The materials according to item (B) were introduced into a mixer and mixed homogeneously. Then the core tablet as produced beforehand was coated with an envelope of this mixture, the coating procedure being performed in a known per se manner by means of so-called compression coating. The resulting envelope was then pan coated with the solution according to item (D) to thus form an outer film that was resistant to gastric juice.

The tablets were shown to be gastric juice resistant, and the manner in which the substances were dissolved out was studied. All this was done by means of techniques analogues to those of Examples 1 and 3. The results are set forth in Table 4.

TABLE 4

DSCG and allergen (Brilliant Blue) dissolved out from gastric juice resistant double tablet in intestinal juice at 37° C.

| | % dissolved out | |
|---|---|---|
| Time, minutes | DSCG | allergen measured as Brilliant Blue |
| 5 | 9 | — |
| 10 | 52 | — |
| 15 | 75 | — |
| 20 | 90 | 12 |
| 30 | 101 | 93 |
| 40 | — | 97 |

I claim:

1. A formulated preparation for oral administration and ingestion containing an immunotherapeutically active amount of at least one allergen, which preparation
   (i) is resistant to gastric juice and contains in addition to said at least one allergen a therapeutically active amount of an anti-allergic substance that will inhibit an allergen induced IgE-mediated allergic and inflammatory reaction,
   (ii) being composed of at least one inner core containing the allergen and of an outer envelope which surrounds and confines said at least one core and which contains said anti-allergic substance, and
   (iii) being formulated so that upon being administed it gives a delayed release of both said active amount of antiallergic substance and said immunotherapeutic amount of allergen in a manner such that said two amounts are released in the said order under the action of intestinal juice, but not under the action of gastric juice, said allergen being allergenic in the sense that it is able to mount an immune response in a mammal resulting in antibody of the IgE-class and that it is able to trigger an allergic reaction when the mammal is later exposed to the allergen.

2. A preparation according to claim 1 in which said envelope is coated with a gastric juice resistant film.

3. A preparation according to claim 1 in which each core is coated with a gastric juice resistant film.

4. A preparation according to claim 1 in the form of a capsule or tablet.

5. A preparation according to claim 1 in which said anti-allergic substance is an inhibitor for mediator release.

6. A preparation according to claim 2 in which said anti-allergic substance is an inhibitor for mediator release.

7. A preparation according to claim 3 in which said anti-allergic substance is an inhibitor for mediator release.

8. A preparation according to claim 1 from which said active amount of anti-allergic substance and said immunotherapeutic amount of allergen are released within 60 and 120 minutes, respectively, under the action of intestinal juice.

9. A preparation according to claim 4 in which said allergic substance is a bis-chromonyl compound.

10. A method for intestinal immunotherapy treatment of IgE mediated allergy which comprises orally administering an immunotherapeutic amount of at least one allergen, characterized by administering a formulated preparation which is
   (i) resistant to gastric juice and contains in addition to said at least one allergen a therapeutically active amount of an anti-allergic substance that will inhibit an allergen induced IgE-mediated allergic and inflammatory reaction,
   (ii) composed of at least one inner core containing the allergen and of an outer envelope which surrounds and confines said at least one core and contains said anti-allergic substance, and
   (iii) formulated so that upon being administered it gives a delayed release of both said active amount of anti-allergic substance and said immunotherapeutic amount of allergen in a manner such that said two amounts are released in the said order under the action of intestinal juice, but not under the action of gastric juice,
   said allergen being allergenic in the sense that it is able to mount an immune response in a mammal resulting in antibody of the IgE-class and that it is able to trigger an allergic reaction when the mammal is later exposed to the allergen.

* * * * *